(12) United States Patent
Hoffman et al.

(10) Patent No.: US 6,173,031 B1
(45) Date of Patent: Jan. 9, 2001

(54) DETECTOR MODULES FOR COMPUTED TOMOGRAPH SYSTEM

(75) Inventors: David M. Hoffman, New Berlin; Brian D. Johnston, Oconomowoc, both of WI (US); Francois Kotian, Bois d'Arcy (FR); Hui David He, Waukesha, WI (US)

(73) Assignee: General Electric Company, Milwaukee, WI (US)

( * ) Notice: Under 35 U.S.C. 154(b), the term of this patent shall be extended for 0 days.

(21) Appl. No.: 08/977,442

(22) Filed: Nov. 26, 1997

(51) Int. Cl.⁷ .................................................. G01N 23/00
(52) U.S. Cl. ............................. 378/19; 250/370.09
(58) Field of Search ..................... 378/19; 250/370.11, 250/370.109

(56) References Cited

U.S. PATENT DOCUMENTS 4,338,521 * 7/1982 Shaw et al. ...................... 250/370.11
4,965,726   10/1990 Heuscher et al. .
5,592,523   1/1997 Tuy et al. .

FOREIGN PATENT DOCUMENTS 6-169912 * 6/1994 (JP) ........................................ 378/19

* cited by examiner

Primary Examiner—Craig E. Church
(74) Attorney, Agent, or Firm—Armstrong Teasdale; Christian G. Cabou; Phyllis Y. Price

(57) ABSTRACT

A multislice detector module producing an alterable quantity of slices and slice resolutions. In one embodiment, the detector module includes a plurality of photodiodes arranged in an array of rows and columns, a switch apparatus electrically coupled to photodiode output signals, and a decoder. The decoder is configured to enable or prevent each photodiode from being transmitted through the switch apparatus. The configuration of the decoder determines how many slices of data are transmitted and the resolution of each slice.

14 Claims, 3 Drawing Sheets

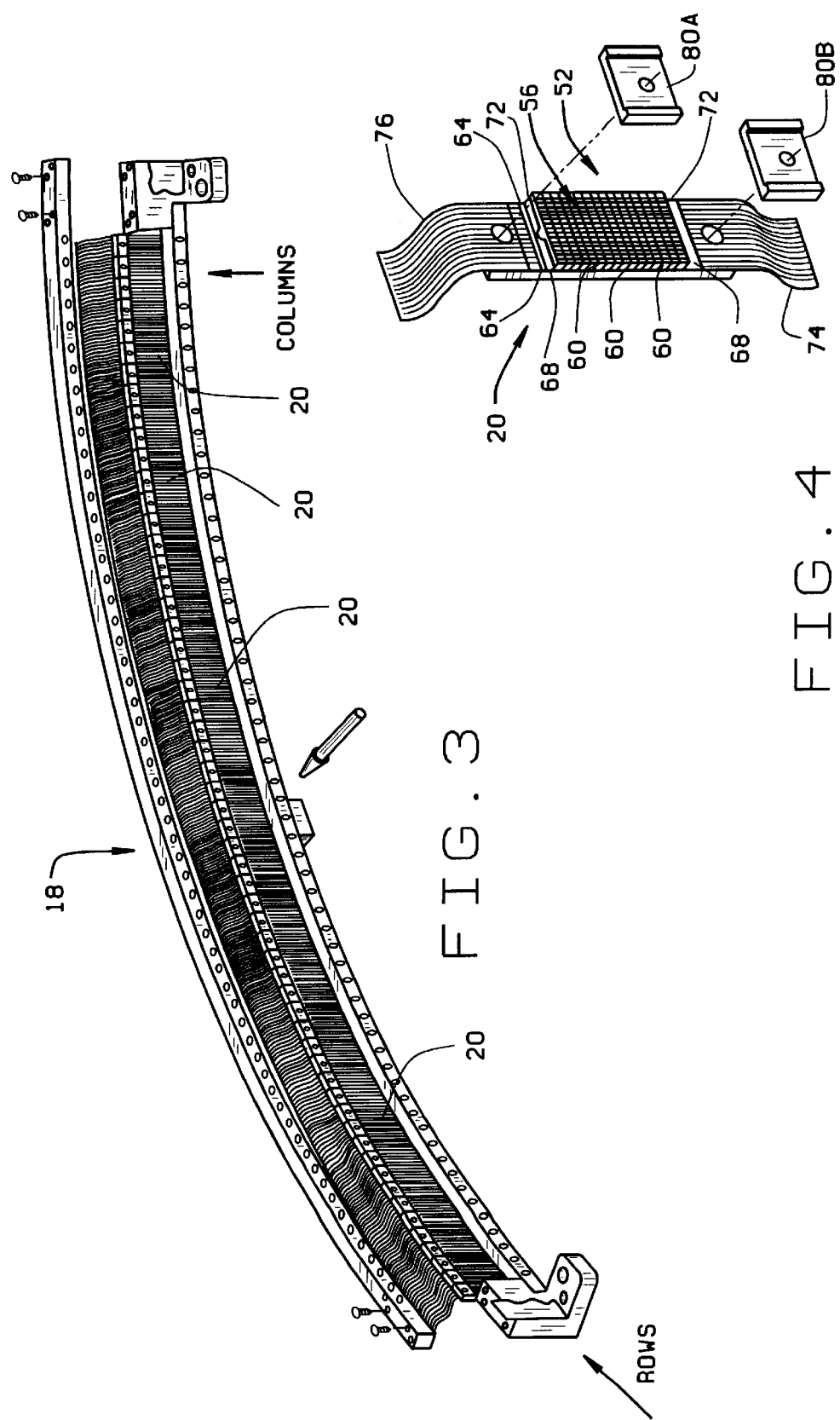

DETECTOR MODULES FOR COMPUTED TOMOGRAPH SYSTEM

FIELD OF THE INVENTION

This invention relates generally to computed tomograph (CT) imaging and, more particularly, to detector modules utilized in connection with CT systems.

BACKGROUND OF THE INVENTION

In at least some computed tomograph (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector. A scintillator is located adjacent the collimator, and photodiodes are positioned adjacent the scintillator.

Multislice CT systems are used to obtain data for an increased number of slices during a scan. Known multislice systems typically include detectors generally known as 3-D detectors. With such 3-D detectors, a plurality of detector elements form separate channels arranged in columns and rows. Each row of detectors forms a separate slice. For example, a two slice detector has two rows of detector elements, and a four slice detector has four rows of detector elements. During a multislice scan, multiple rows of detector cells are simultaneously impinged by the x-ray beam, and therefore data for several slices is obtained.

Multislice detectors generate much more data than single slice detectors. This increased data generation capability is not, however, always required or desired. For example, a variety of tests performed by a CT system do not require high slice quantity or high slice resolution. Also, with such large amounts of data being collected, the time required to perform a scan may increase, resulting in higher costs and lower throughput.

Accordingly, it would be desirable to provide a detector module that allows data to transmitted from an alterable number of slices to accommodate the specific needs of a test. In addition, it is desirable to provide a detector module having an alterable slice resolution.

SUMMARY OF THE INVENTION

These and other objects may be attained by a detector module which, in one embodiment, enables modification of the quantity of slices and slice resolution, or slice thickness. The detector module includes a photodiode array optically coupled to a scintillator array. The photodiode array includes a plurality of photodiodes arranged in rows and columns. A collimator array is aligned and positioned adjacent to the scintillator array to collimate the x-ray beams.

The detector module further includes a switch apparatus and a decoder. The switch apparatus is electrically coupled between the photodiode output lines and a CT system data acquisition system (DAS). The switch apparatus, in one embodiment, is an array of FETs and alters the number of slices and the thickness of each slice by allowing each photodiode output line to be enabled, disabled, or combined with other photodiode output lines.

More specifically, after an operator has determined the desired number of slices and slice thickness, the appropriate switch apparatus configuration is electrically transmitted from the CT system computer to the decoder, e.g., via a flexible cable. The appropriate decoder output lines are then connected to the switch apparatus control lines so that data is transmitted from the photodiodes output lines in the selected configuration.

In one embodiment, the detector module is fabricated by depositing, or forming, the photodiode array, the switch apparatus, and the decoder on a substrate. Each photodiode output line is electrically connected to the switch apparatus inputs, and each switch apparatus output and each decoder control line are then electrically coupled to the first end of a flex cable. After installing the detector modules into the detector array, the second end of the flex cable is electrically connected to the CT system data acquisition system (DAS).

The above described detector module enables selection of the number of slices of data to be electrically transmitted for each rotation of the CT system. In addition, the detector module allows the slice thickness to be selected to produce various slice resolutions. As a result, the configuration of the detector module can be altered to accommodate the specific needs and requirements of the test.

BRIEF DESCRIPTION OF THE DRAWINGS

FIG. 3 is a perspective view of a detector array in accordance with the present invention.

FIG. 4 is a perspective view of a detector module in accordance with the present invention.

DETAILED DESCRIPTION

Figure 1:
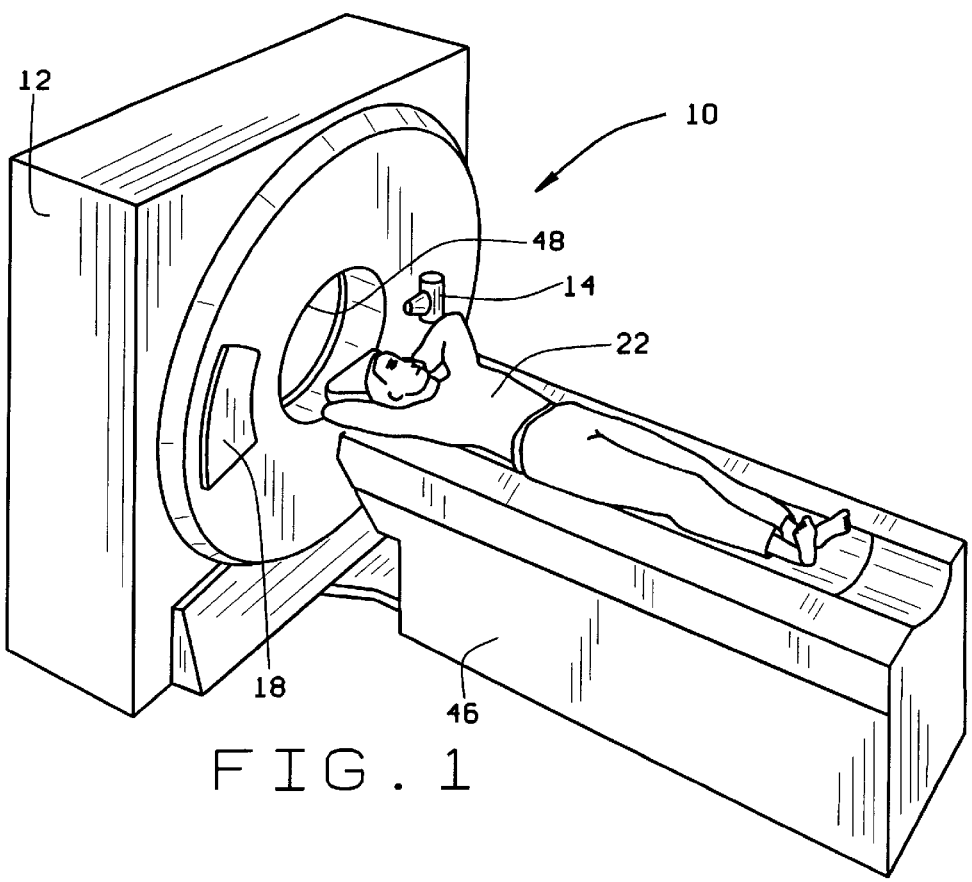
FIG. 1 is a pictorial view of a CT imaging system.
Figure 2:
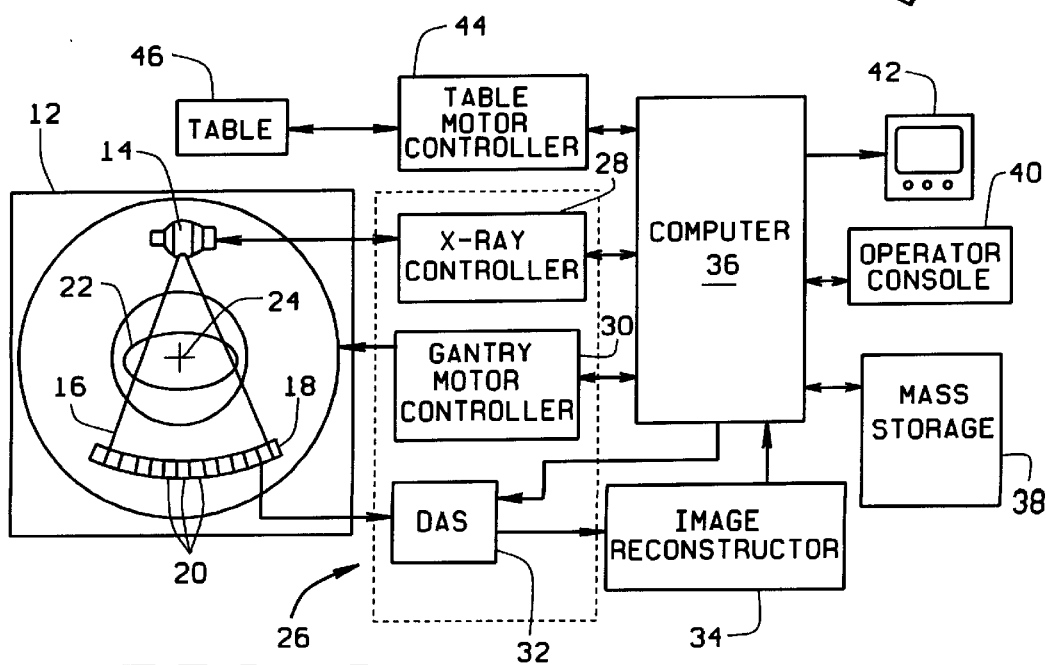
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector modules 20 which together sense the projected x-rays that pass through a medical patient 22. Each detector module 20 produces electrical signals that represent the intensity of impinging x-ray beams and hence the attenuation of the beams as they pass through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10.

Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector modules 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through a gantry opening 48.

As shown in FIGS. 3 and 4, detector array 18 includes a plurality of detector modules 20. Each detector module 20 includes a multidimensional photodiode array 52 and a multidimensional scintillator array 56 positioned above and adjacent to photodiode array 52. A collimator (not shown) is positioned above and adjacent scintillator array 56 to collimate x-ray beams 16 before such beams impinge upon scintillator array 56. Photodiode array 52 includes a plurality of photodiodes 60 which are optically coupled to scintillator array 56, and photodiodes 60 generate electrical output signals 64 representative of the light output by each scintillator of scintillator array 56.

In one embodiment, as shown in FIG. 3, detector array 18 includes fifty-seven detector modules 20. Each detector module 20 includes a photodiode array 52 and scintillator array 56, each having an array size of 16×16. As a result, array 18 has 16 rows and 912 columns (16×57 modules) allowing 16 simultaneous slices of data to be collected with each rotation of gantry 12.

Detector module 20 also includes a switch apparatus 68 electrically coupled to a decoder 72. Switch apparatus 68 is a multidimensional semiconductor switch array of similar size as photodiode array 52. In one embodiment, switch apparatus 68 includes an array of field effect transistors (not shown) with each field effect transistor (FET) having an input, an output, and a control line (not shown). Switch apparatus 68 is coupled between photodiode array 52 and DAS 32. Particularly, each switch apparatus FET input is electrically connected to a photodiode array output 64 and each switch apparatus FET output is electrically connected to DAS 32, for example, using flexible electrical cables 74 and 76. Cables 74 and 76 are secured to detector module 20 with mounting blocks 80A and 80B.

Decoder 72 controls the operation of switch apparatus 68 to enable, disable, or combine photodiode outputs 64 in accordance with a desired number of slices and slice resolutions for each slice. Decoder 72, in one embodiment, is a decoder chip or a FET controller as known in the art. Decoder 72 includes a plurality of output and control lines coupled to switch apparatus and computer 36. Particularly, the decoder outputs are electrically connected to the switch apparatus control lines to enable switch apparatus 68 to transmit the proper data from the switch apparatus inputs to the switch apparatus outputs. The decoder control lines are electrically connected to the switch apparatus control lines and determine which of the decoder outputs will be enabled. Utilizing decoder 72, specific FETs within switch apparatus 68 are enabled, disable, or combined so that specific photodiode outputs 64 are electrically connected to CT system DAS 32. In one embodiment defined as a 16 slice mode, decoder 72 enables switch apparatus 68 so that all rows of photodiode array 52 are connected to DAS 32, resulting in 16 simultaneous slices of data are electrically connected to DAS 32. Of course, many other slice combinations are possible.

Figure 5:
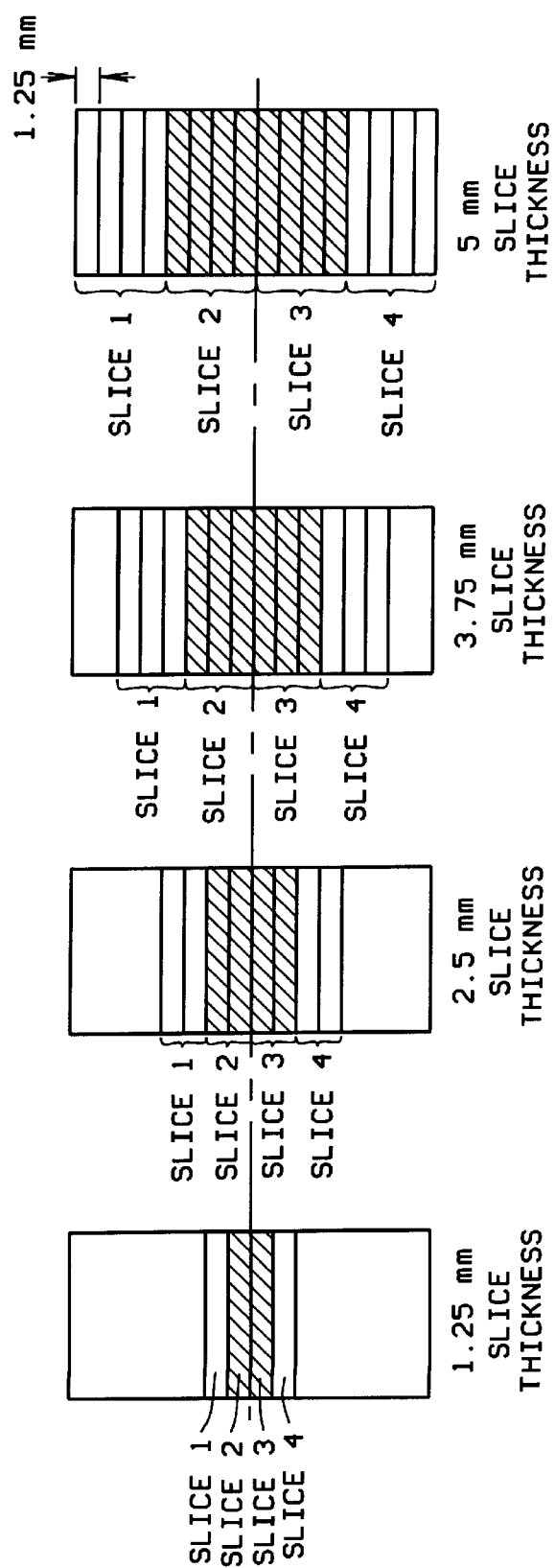
FIG. 5 is various configurations of the detector module in FIG. 4 in a four slice mode.

For example, decoder 72 may also select from other multiple slice modes, including one, two, and four slice modes. As shown in FIG. 5, by transmitting the appropriate decoder control lines, switch apparatus 68 can be configured in the four slice mode so that data is collected from four slices of one or more rows of photodiode array 52. Depending upon the specific configuration of switch apparatus 68 as defined by decoder control lines, various combinations of photodiode outputs 64 can be enabled, disabled, or combined so that the slice thickness may be 1.25 mm, 2.5 mm, 3.75 mm, or 5 mm. Additional examples include, a single slice mode including one slice with slices ranging from 1.25 mm thick to 20 mm thick; and a two slice mode including two slices with slices ranging from 1.25 mm thick to 10 mm thick. Additional modes beyond those described are possible.

Figure 6:
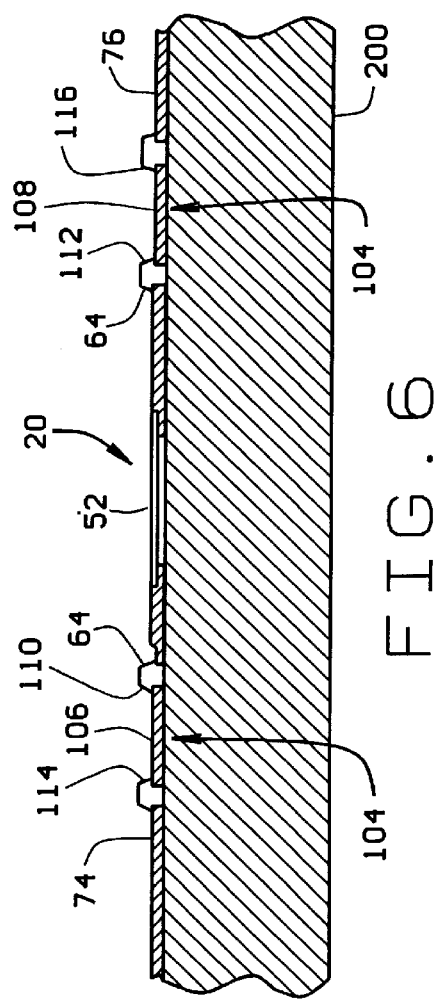
FIG. 6 is a side view of the detector module shown in FIG. 4.

In one embodiment and referring to FIG. 6, switch apparatus 68 and decoder 72 are combined into a FET array 104. FET array 104 includes a plurality of field effect transistors (FET) (not shown) arranged as a multidimensional array. In one embodiment, two semiconductor devices 106 and 108 are utilized so that one-half of photodiode output lines 64 are connected to device 106 and one-half of photodiode output lines 64 are connected to device 108. FET arrays 106 and 108 each include respective input lines 110 and 112, output lines 114 and 116, and control lines (not shown). Internal to device 106, input lines 110 are electrically connected to the switch apparatus input lines, output lines 114 are electrically connected to the switch apparatus output lines, and decoder output lines are electrically connected to FET control lines. Switch 108 is internally configured identical to switch 106.

In fabrication of detector module 20, photodiode array 52 including scintillator array 56 and FET arrays 106 and 108 are deposited, or formed, on substrate 200 in a manner known in the art so that photodiode outputs 64 are adjacent arrays 106 and 108. Photodiode outputs 64 are then connected to inputs 110 and 112 of respective FET arrays 106 and 108. Particularly, one-half of photodiode outputs 64 are wire bonded to FET array inputs 110 and one-half of photodiode outputs 64 are wire bonded to respective PET array inputs 112 so that each output 64 is electrically connected to a FET input line. Photodiode outputs are wire bonded to FET input lines using various wire bonding techniques, including, for example, aluminum wire wedge bonding and gold wire ball bonding as known in the art. First ends of flexible electrical cables 74 and 76 are then electrically connected and secured to FET arrays 106 and 108. FET array output and control lines are electrically connected to cables 74 and 76. Particularly, each FET array output line 114 and 116 is wire bonded to a wire of respective cables 74 and 76. Detector module 20 is completed by securing first ends of cables 74 and 76 with mounting blocks 80A and 80B.

After fabricating detector modules 20 as described above, detector modules 20 are mechanically mounted into array 18. Second ends of cables 74 and 76 of each detector module 20 are then electrically connected to CT system DAS 32. The collimator is then aligned and secured adjacent to scintillator arrays 56.

In operation, the operator determines the number of slices and thickness of each slice. The appropriate configuration information is transmitted to the array control lines to configure switch apparatus 68 using decoder 72. As X-ray beams 16 impinge upon detector modules 20, data for the selected configuration is transmitted to DAS 32.

The above described detector module enables selection of the number of slices of data to be electrically transmitted for each rotation of the CT system. In addition, the detector module allows the slice thickness to be selected to produce various slice resolutions. As a result, the configuration of the detector module can be altered to accommodate the specific needs and requirements of the test.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. Accordingly, the spirit and scope of the invention are to be limited only by the terms of the appended claims.

What is claimed is:

1. A detector module for a computed tomograph machine, said detector module comprising:
   a collimator array;
   a scintillator array adjacent said collimator array;
   a photodiode array optically coupled to said scintillator array;
   switch apparatus electrically coupled to said photodiode array; and
   a decoder coupled to said switch apparatus,
   said decoder configured to control operation of said switch apparatus to combine data signals in accordance with a selected number of slices and slice thickness and to select a number of slices of data transmitted during detection of the data from the detector module.

2. A detector module in accordance with claim 1 wherein said decoder controls said switch apparatus to selectively operate in a plurality of slice modes.

3. A detector module in accordance with claim 1 wherein each of said scintillator array and said photodiode array are 16×16 arrays.

4. A detector module in accordance with claim 3 wherein said switch comprises an array of transistors.

5. A detector module in accordance with claim 3 wherein for a four slice mode, a selected slice thickness comprises at least one row.

6. A method for controlling operation of a detector module in a computed tomograph machine, the module including a scintillator array, a photodiode array optically coupled to the scintillator array, and a switch apparatus electrically coupled to the photodiode array, said method comprising the steps of:
   configuring the switch apparatus to combine data signals in accordance with a desired number of slices;
   configuring the switch apparatus to combine data signals to provide a desired slice thickness for each slice; and
   configuring the switch apparatus to transmit, during detection of data, the desired number of slices of data.

7. A method in accordance with claim 6 wherein configuring the switch apparatus in accordance with a desired number of slices comprises the step of selecting at least one of a plurality of modes.

8. A method in accordance with claim 7 wherein for a four slice mode, a selected slice thickness can be selected as of at least one row.

9. A detector module for a computed tomograph machine, said detector module comprising:
   a collimator array;
   a scintillator array adjacent said collimator array;
   a photodiode array optically coupled to said scintillator array;
   switch apparatus electrically coupled to said photodiode array, said switch apparatus comprising an array of field effect transistors; and
   a decoder coupled to said switch apparatus,
   said decoder configured to control operation of said switch apparatus to combine data signals in accordance with a selected number of slices and slice thickness, said switch apparatus to selectively operate in a plurality of slice modes and to select a number of slices of data to transmit during detection of the data from said detector module.

10. A detector module in accordance with claim 9 wherein each of said scintillator array and said photodiode array are 16×16 arrays.

11. A detector module in accordance with claim 10 wherein said switch comprises an array of transistors.

12. A detector module in accordance with claim 10 wherein for a four slice mode, a selected slice thickness comprises at least one row.

13. A detector module in accordance with claim 1 further comprising a substrate, and wherein said scintillator array, said photodiode array, said switch apparatus, and said decoder reside of said substrate.

14. A detector module in accordance with claim 9 further comprising a substrate, and wherein said scintillator array, said photodiode array, said switch apparatus, and said decoder reside on said substrate.

* * * * *

UNITED STATES PATENT AND TRADEMARK OFFICE
CERTIFICATE OF CORRECTION

PATENT NO. : 6,173,031 B1
DATED : January 9, 2001
INVENTOR(S) : Hoffman, et al.

It is certified that error appears in the above-identified patent and that said Letters Patent is hereby corrected as shown below:

<u>Claim 13, column 6,</u>
Line 49, delete "of" and substitute -- on --.

Signed and Sealed this

Twenty-fifth Day of September, 2001

Attest:

*Nicholas P. Godici*

NICHOLAS P. GODICI
*Attesting Officer*     *Acting Director of the United States Patent and Trademark Office*